United States Patent
Yamazaki et al.

(10) Patent No.: US 7,005,053 B2
(45) Date of Patent: Feb. 28, 2006

(54) MULTI-CAPILLARY ELECTROPHORESIS APPARATUS

(75) Inventors: Motohiro Yamazaki, Mito (JP); Masaya Kojima, Mito (JP); Ryoji Inaba, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 440 days.

(21) Appl. No.: 10/252,557

(22) Filed: Sep. 24, 2002

(65) Prior Publication Data

US 2003/0116438 A1   Jun. 26, 2003

(30) Foreign Application Priority Data

Dec. 20, 2001 (JP) .............................. 2001-387008

(51) Int. Cl.
  *G01N 27/453* (2006.01)
(52) U.S. Cl. ..................................... 204/602; 204/601
(58) Field of Classification Search ........ 204/601–605, 204/621

See application file for complete search history.

(56) References Cited

U.S. PATENT DOCUMENTS 5,736,025 A * 4/1998 Smith et al. ................ 204/621
5,788,566 A * 8/1998 McAnally et al. .......... 454/184
6,572,750 B1 * 6/2003 Cong et al. ................. 204/453

FOREIGN PATENT DOCUMENTS

| JP | 4-231862 | 8/1992 |
| JP | 10-206384 | 8/1998 |
| JP | 2001-99813 | 4/2001 |

OTHER PUBLICATIONS

JPO computer translation of Muneo et al. (JP 2001-099813 A).*

* cited by examiner

*Primary Examiner*—Alex Noguerola
(74) *Attorney, Agent, or Firm*—Dickstein Shapiro Morin & Oshinsky LLP

(57) ABSTRACT

Scattering on analysis in a multi-capillary electrophoresis apparatus is suppressed. The multi-capillary electrophoresis apparatus has a multi-capillary array that has a sample and a separation medium for separating a sample charged therein, and has a sampling section formed at ends of the capillaries and a detector part for acquiring information depending on the sample thus separated, a means for applying a voltage between the sampling section and the detector part, a chamber part having an air blowing mechanism and a temperature controlling mechanism, a capillary housing base provided on a leeward side of the air blowing mechanism and housing the multi-capillary array, and a first straightening plate provided between the chamber part and the capillary housing base.

32 Claims, 10 Drawing Sheets

MULTI-CAPILLARY ELECTROPHORESIS APPARATUS

BACKGROUND OF THE INVENTION

1. Field of the Invention

The present invention relates to an electrophoresis apparatus capable of separating components in a sample by electrophoresis, and more particularly, it relates to a multi-capillary electrophoresis apparatus having plural capillaries.

2. Description of the Related Art

DNA sequencing has been conventionally carried out by a slab gel method, in which a gel for separating a sample is sandwiched with two sheets of transparent glass plate, and a voltage is applied to both ends of the glass plates to effect electrophoresis. JP-A-7-301619, JP-A-8-297111 and JP-A-9-288091 disclose techniques for uniformly maintaining the temperature of the gel within the slab.

An electrophoresis apparatus of the slab gel method disclosed in JP-A-7-301619 has two sheets of transparent glass plates with a thermal control plate, a Peltier element attached in contact with the back surface thereof, a heat sink attached to the heat dispersion surface of the Peltier element, and a cooling fan dispersing the heat of the heat sink.

In the technique disclosed in JP-A-8-297111, a glass plate and a member having good heat conductivity are provided with both of them being in close contact with each other, and the periphery of the assembly is surrounded with a thermal insulation material, whereby heat dispersion is prevented, and the temperature of the glass plates is uniformly maintained.

The technique disclosed in JP-A-9-288091 involves a gel, a light transmission flat plate for maintaining the gel, a pair of a temperature adjusting element and a temperature controlling element for controlling the temperature adjusting element arranged on both sides of the flat plate, upper and lower buffer solution vessels in contact with the gel and the flat plate, and electrodes immersed in buffer solutions charged in the buffer solution vessels. The temperature of the buffer solution arbitrarily and precisely controls the temperature of the gel.

In recent years, a capillary electrophoresis apparatus is being widely spread. A temperature controlling technique used for the capillary electrophoresis apparatus has been disclosed in JP-A-9-251000, JP-A-10-206384 and JP-A-11-277125.

In the capillary electrophoresis apparatus, electrophoresis is carried out in a capillary tube. The capillary tube is a thin tube having an inner diameter of several tens of $\mu$m, an outer diameter of a hundred of $\mu$m, and a length of several hundreds of mm. A gel (separating medium) is charged in the pore of the capillary tube, and a testing sample to be measured is introduced into the gel. A high voltage of about several tens of kV is applied to both ends of the capillary tube to effect electrophoresis of the testing sample. For example, fluorescence excited upon irradiating the testing sample with excitation light is detected with a photodetector to effect analysis of the testing sample. A DNA fragment sample with a primer or a terminator labeled with a fluorescent substance, for example, by using the Sanger-Coulson method, is subjected to electrophoresis, and fluorescence from the sample during the electrophoresis is detected to determine the base sequence of the DNA. Such an apparatus is referred to as a DNA base sequence analysis apparatus (DNA sequencer).

In order to improve reproducibility of measurement on electrophoresis, and to improve separation performance for testing samples, it is necessary that the electrophoresis conditions, such as the applied voltage and the composition of the gel, are maintained at constant values. However, the electrophoresis temperature that provides the optimum separation conditions varies depending on difference in sample to be analyzed and difference in separation method. In order to maintain the temperature of the gel in the capillary container part uniformly at a constant value without depending on the outside air temperature and the positions, a thermostat oven or the like may be used.

As another reason why the temperature control is necessary, there is a demand for improvement in throughput. The separation time is being demanded to be shortened owing to increase of the amount of gene to be analyzed along with technological progress in recent years, and thus, the applied voltage to the capillary is being increased. On another front, the amount of Joule heat produced is increased on applying such a high voltage to increase the temperature of the gel, and thus the temperature control becomes further difficult.

In the technique disclosed in JP-A-9-251000, the side surface of the capillary is covered with a transparent member that is a prescribed material having the substantially same refraction index as the capillary, and a temperature controlling means (such as a Peltier element and a heat sink), which maintains the temperature of the sample in the capillary at a substantially constant value, is provided in contact with the transparent member.

The technique disclosed in JP-A-10-206384 uses an air thermostat oven. As a temperature controlling mechanism for maintaining the container part housing a capillary at a constant temperature, a chamber surrounded with a thermal insulation material, such as expanded polyurethane, and a Peltier element are provided. Electrical heating and electrical cooling are carried out by the Peltier element. A fan for forming forced convection is provided in the chamber. A temperature sensor, such as a platinum resistance and a thermocouple, is provided in the chamber, and an output signal detected by the temperature sensor is subjected to feedback to the Peltier element to carry out PID control, whereby the interior of the electrophoresis chamber is maintained at a constant temperature.

The technique disclosed in JP-A-11-277125 uses the similar air thermostat oven as the foregoing technique, and a fan for circulating the air has an aspiration inlet for aspirating the air in the direction of the rotation axis and a blowing outlet for blowing the air in the radial direction. The characteristic feature of the technique is that the fan is provided in such a manner that the thickness direction of the fan agrees with the thickness direction of the air thermostat oven.

Furthermore, JP-A-2001-99813 discloses a technique, in which air in a thermostat oven is circulated, and a wall of an air circulation channel is formed with a material of good thermal conduction, and JP-A-4-231862 discloses a capillary electrophoresis apparatus, in which a uniform air flow is formed in a thermostat oven, and a heat exchanger is provided on the circulation channel.

The slab gel method, the temperature controlling mechanism for an electrophoresis apparatus of the single capillary method, and the temperature controlling mechanism for an apparatus using the air thermostat oven have been described.

In the technique disclosed in JP-A-7-301619, the Peltier element does not cover the entire surface of the glass plate. Therefore, the region that can be controlled for the temperature thereof is limited to local area. In the technique disclosed in JP-A-8-297111, only the amount of dispersed heat due to the Joule heat caused by electrophoresis is adjusted, but there is a problem in that temperature control is carried out by providing a heat source for heating.

Such a technique is demanded in recent years that electrophoresis is carried out by using plural capillaries simultaneously to improve processing performance. In the techniques disclosed in JP-A-9-288091 and JP-A-9-251000, there is limitation in increasing the number of capillaries, and the number of samples that can be simultaneously analyzed is limited. In other words, there is a problem on applying the technique of sandwiching capillaries with plates of plane heat sources to a multi-capillary electrophoresis apparatus that analyzes plural samples at the same time.

A commercially available microtiter plate has 96 holes (hereinafter referred to as a "well"). In the case where samples to be analyzed are set in the wells of the microtiter plate, 96 wells are arranged in a matrix form of 8 rows and 12 columns. It is general that, in the samples put in the wells arranged in the matrix form, the samples in one row among the 8 rows or the samples in one column among the 12 columns are simultaneously analyzed. According to the operation, a bundle of the plural capillaries (hereinafter referred to as a "capillary array" or a "multi-capillary array"), to which the samples are introduced for carrying out electrophoresis, can be arranged in one plane. Therefore, the temperature control can be carried out by applying the technique of sandwiching the capillaries with plates of plane heat sources.

However, in the case where more than 12 samples are necessarily analyzed at the same time, or in the case where all the samples set in the microtiter plate having 96 wells are necessarily introduced to a capillary array and subjected to electrophoresis, 12 wells in one row in the microtiter plate are insufficient, and therefore, the samples in several rows or several columns are simultaneously introduced in the capillary array for analysis. It is impossible in this case to arrange the sampling sections on one plane. Therefore, it is impossible to employ the technique of sandwiching capillaries with plates of plane heat sources, but it is necessary to carry out temperature control by arranging the capillary array in a steric space, such as a thermostat oven.

Joule heat is formed from the gel itself upon electrophoresis. When the number of capillaries becomes larger, the influence of the Joule heat cannot be negligible. In the presence of a heat generating body, the heat transfer coefficient varies due to differences of the flowing direction and the flowing velocity of the air around the body. Therefore, there is such a problem upon using the ordinary air circulation thermostat oven that the temperature of the capillaries is differentiated with respect to the positions.

In the technique disclosed in JP-A-10-206384, the fan arranged inside the thermostat oven is positioned at the substantially central part of the thermostat oven. Therefore, it cannot provide a uniform air flow velocity distribution in the thermostat oven for forming a uniform temperature distribution by forced convection.

The technique disclosed in JP-A-11-277125 uses a microtiter plate. It is necessary to increase the thickness of the thermostat oven in the case where the number of capillaries that are simultaneously used is increased. Therefore, the radiation heat from the plates having good thermal conduction is insufficient in the plane air circulation method, and thus there is a problem in that the temperature difference occurs with respect to the positions.

SUMMARY OF THE INVENTION

An object of the invention is to provide air flow having a prescribed flow rate around capillaries.

The invention relates to, as one aspect, a multi-capillary electrophoresis apparatus having a multi-capillary array containing plural capillaries having a separation medium for separating a sample, and a thermostat oven housing at least a part of the multi-capillary array and having a air blower and a temperature controlling mechanism, and the apparatus further has a straightening plate having a prescribed opening.

By using the straightening plate, the air flow formed by the air blowing mechanism and the temperature controlling mechanism provides a prescribed velocity around the capillary array. As a result of the configuration, the difference of the temperatures of the capillaries can be suppressed.

BRIEF DESCRIPTION OF THE DRAWINGS

FIGS. 3A to 3C are diagrams showing the structures of the air thermostat ovens in the electrophoresis apparatus according to one embodiment of the invention, in which FIG. 3A is a side cross sectional view of the air thermostat oven, FIG. 3B is a front elevational view of the air thermostat oven, and FIG. 3C is a side cross sectional view of a modified example of the air thermostat oven of FIG. 3A.

FIGS. 4A to 4C are diagrams showing the structures of the air blowing fans provided inside the air thermostat oven in the electrophoresis apparatus according to one embodiment of the invention, in which FIG. 4A is a diagram showing the structure of the axial flow fan, FIG. 4B is a diagram showing the structure of the cross flow fan, and FIG. 4C is a diagram showing the structure of the blades of the cross flow fan.

FIGS. 6A and 6B are diagrams showing the air flow inside the air thermostat oven using an axial flow fan, in which FIG. 6A is a diagram showing the side view of the air flow, and FIG. 6B is a diagram showing the front view of the air flow.

FIGS. 7A and 7B are diagrams showing the air flow inside the air thermostat oven using a cross flow fan, in which FIG. 7A is a diagram showing the side view of the air flow, and FIG. 7B is a diagram showing the front view of the air flow.

DESCRIPTION OF THE PREFERRED EMBODIMENTS

The inventors have contemplated for the relationship of the temperature and the flow rate of the air flow with respect to the temperature of the capillaries.

Figure 1:
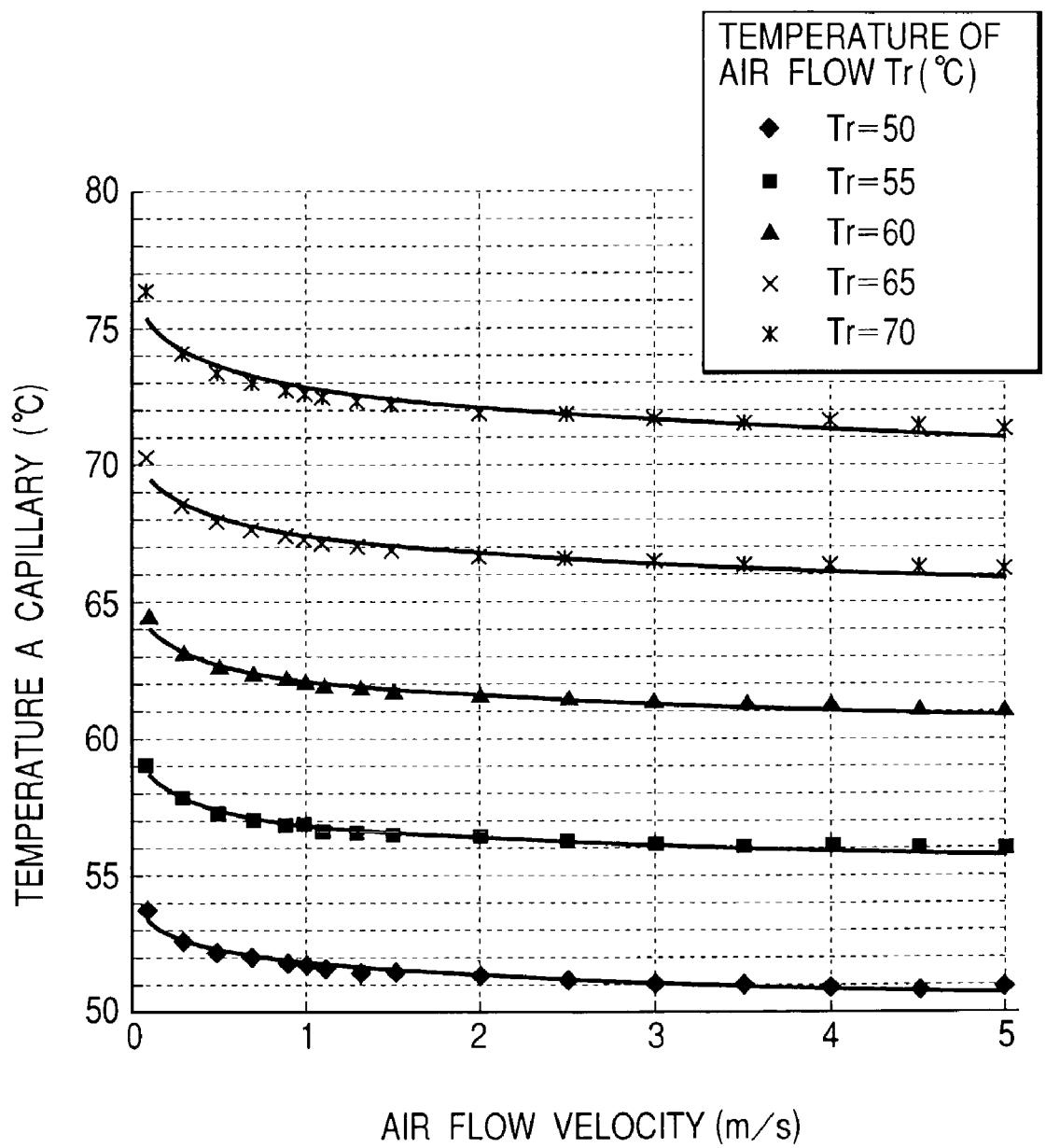
FIG. 1 is a graph showing the relationship between the air flow velocity and the capillary temperature in the multi-capillary electrophoresis apparatus.

FIG. 1 shows the relationship of the temperature Tr (° C.) and the flow rate of the air flow, and the temperature of the capillaries in the multi-capillary array according to one embodiment of the invention. The abscissa indicates the velocity (m/s) of the air circulation flow, and the ordinate indicates the temperature (° C.) of the capillaries. The relationship between the flow rate of the air flow and the temperature of the capillaries is shown for the respective cases where the temperature of the air circulation flow is 50, 55, 60, 65 and 70° C.

In order to assure the sufficient resolution on analysis, it is considered that the positional difference of the temperature of the capillaries is necessarily suppressed to 3° C. or less. Upon forming stagnation, such as vortex flow, in the air flow in contact with the capillaries, however, the air flow velocity is fluctuated within a considerable range (for example, from 0 to 5 m/s), and therefore, the temperature of the capillaries is not uniform due to the difference of the air flow velocity, as understood from FIG. 1.

Under the circumstances, the inventors have considered that in order to assure uniformity of the temperature of the capillaries, it is necessary to apply an air flow having a flow rate as large as possible to the entire capillaries. This is because the difference of the temperature of the capillaries due to the difference in flow rate of the air flow in contact with the capillaries can be decreased with an air flow having a large flow rate.

For example, in the case where the temperature of the air flow is 60° C., the difference of the velocity of the air flow is assumed to be 2 m/s. In the case where an air flow having a flow rate of 4 m/s is to be formed, the range of the actual flow rate of the air flow is from 3 to 5 m/s to cause a difference of the temperature of the capillaries of 0.3° C. However, in the case where an air flow having such a low flow rate of about 1 m/s is to be formed, the range of the actual flow rate of the air flow is from substantially zero to 2 m/s to expand the temperature difference to 3° C. or more. Accordingly, when the velocity of the air flow to be applied to the capillaries is larger, the temperature difference of the capillaries becomes smaller. In particular, an air flow having a flow rate of 2 m/s or more is preferred.

In order to apply an air flow having a large flow rate to the entire capillaries, for example, the air flow is applied by using a fan having the same projected area as the part, in which the capillaries are contained. In this case, however, the size of the apparatus becomes larger.

In order to assure the resolution of analysis, an air flow having a uniform flow rate distribution is to be applied to the capillaries. Therefore, in the case where an air circulation channel connecting the capillaries and the fan is designed, and the air circulation channel connecting the fan and the capillaries has a curved part, it is considered that the curvature of the curved part is necessarily such a small value of 7° or smaller with respect to the air flow direction in order to introduce a uniform air flow having a uniform flow rate distribution to the entire capillaries. This is because detachment of the air flow is to be prevented. In this case, however, the size of the air flow channel itself becomes large.

In order to control the temperature of the air flowing in the thermostat oven, it is also considered that the temperature of the interior of the capillaries is monitored, and then the temperature of the air flowing in the thermostat oven is controlled. While such an operation is not impossible, however, an expensive thermometer is necessary for accurate measurement of the temperature inside the tube having an inner diameter of 50 μm, and the thermometer is necessarily set upon installing the capillary array to the electrophoresis apparatus by the user accordingly. Therefore, the apparatus involves difficulties in operation.

Under the circumstances, the inventors have considered that when an air flow is applied to a multi-capillary array having plural capillaries through a straightening plate, such an air flow that does not have differences in air flow velocity and air flow direction exceeding prescribed values can be applied to the capillaries, whereby the temperature differences of the plural capillaries in the longitudinal direction and the radial direction can be suppressed. In other words from another standpoint, it has been considered that the formation of vortex flow in the capillary container part is prevented as much as possible by using the straightening plate, whereby such an air flow velocity can be assured that makes the temperature of the capillaries substantially equivalent to the temperature of the air having been controlled. In particular, it is preferred that the multi-capillary array, which has the prescribed thickness and is difficult to be arranged in the same plane, is aligned and arranged in a virtual flat plate having the prescribed thickness, and such a straightening plate is used that is arranged in substantially parallel with the surface perpendicular to the thickness direction of the virtual flat plate.

Figure 2A:
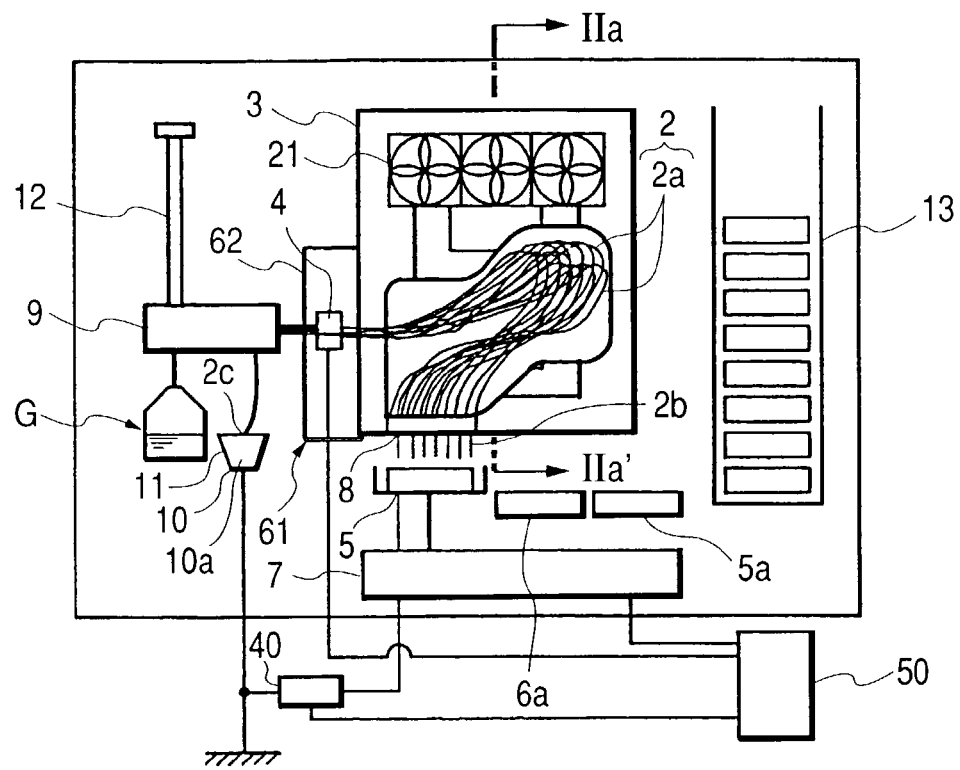
FIG. 2A is a schematic diagram showing the electrophoresis apparatus according to one embodiment of the invention.
Figure 2B:
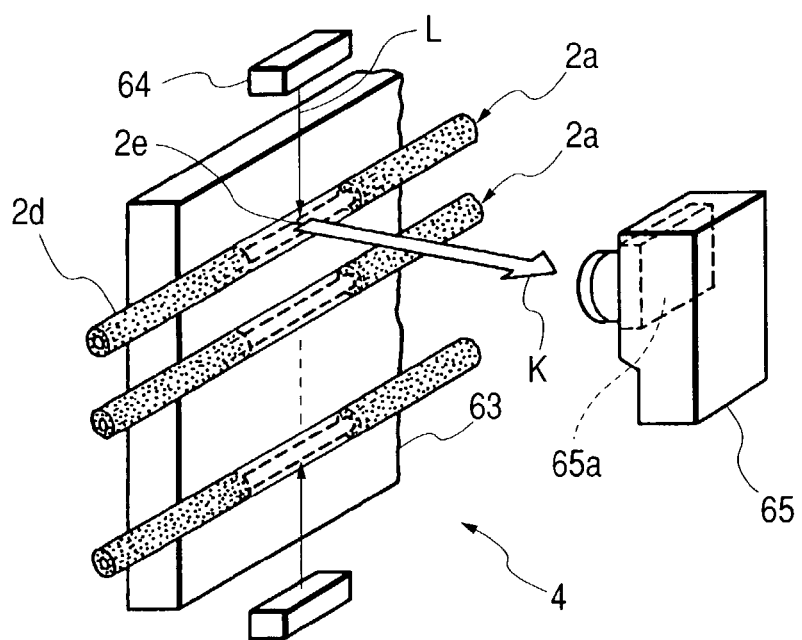
FIG. 2B is a diagram showing the structure of the detecting part of the electrophoresis apparatus.
Figure 3A:
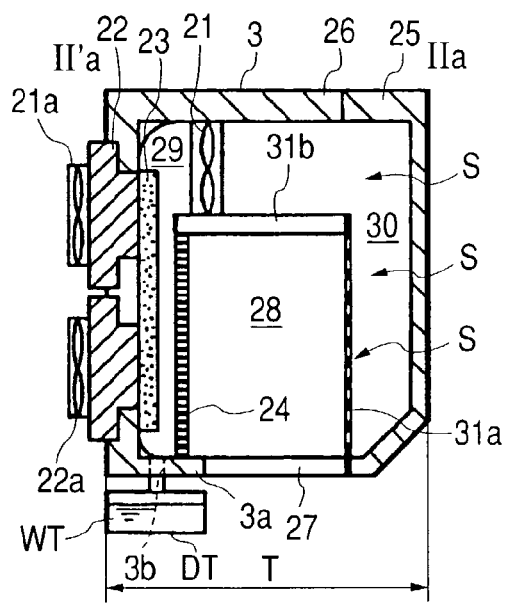
Figure 3B:
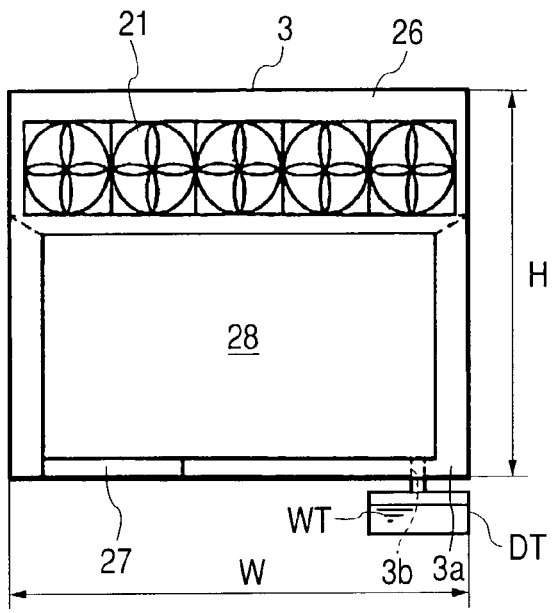
Figure 3C:
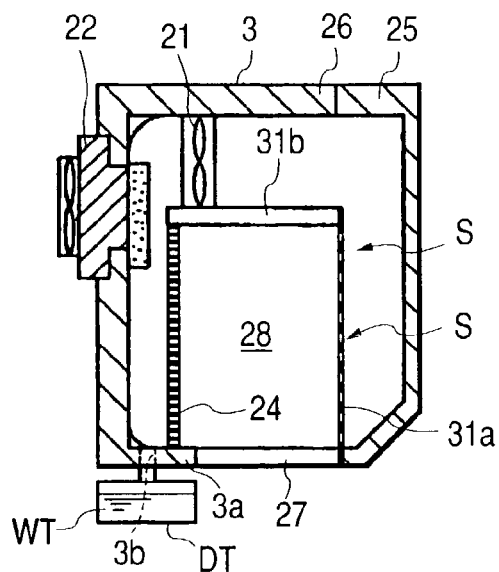
Figure 4A:
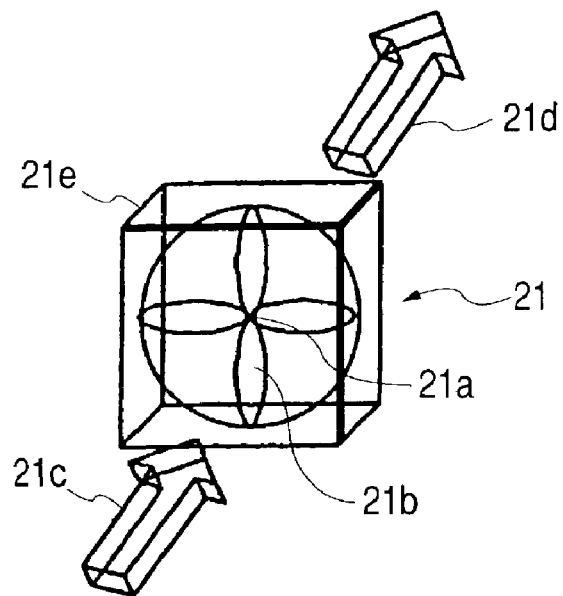
Figure 4B:
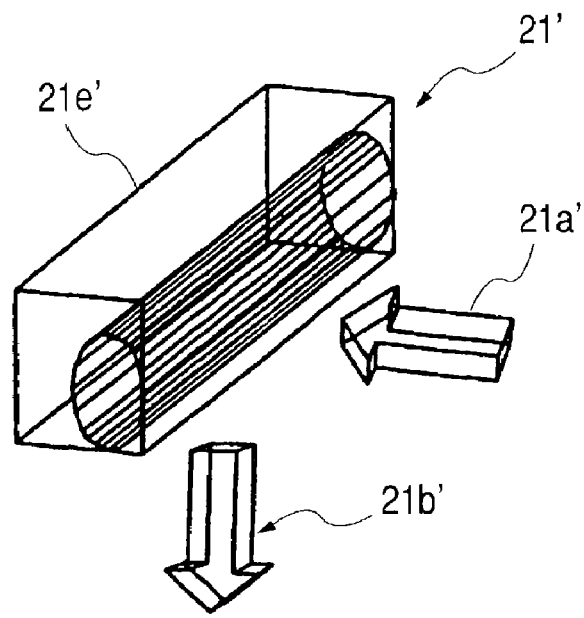
Figure 4C:
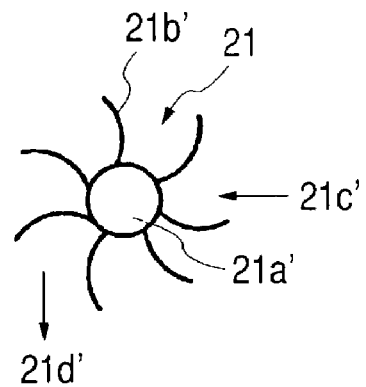
Figure 5A:
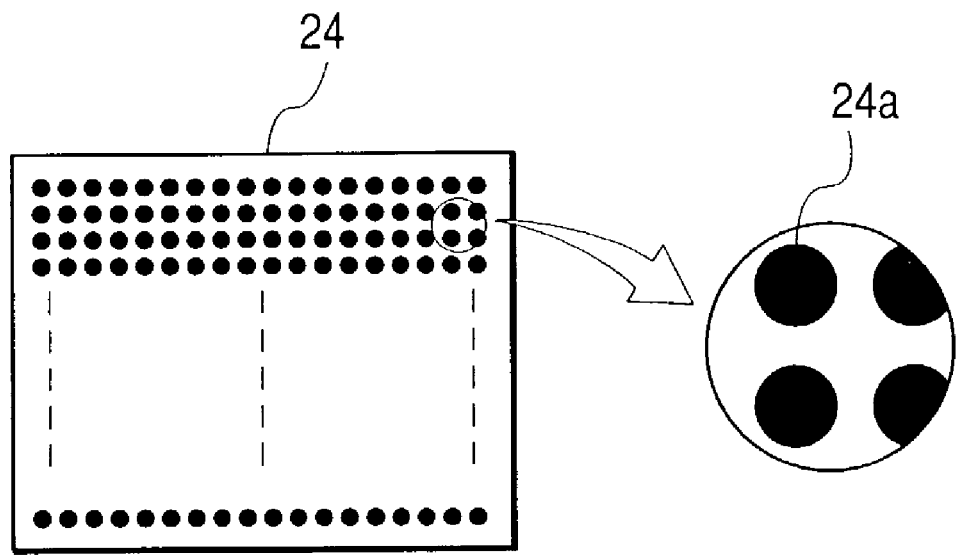
FIGS. 5A and 5B are diagrams showing the structures of the straightening plate provided inside the air thermostat oven in the electrophoresis apparatus according to one embodiment of the invention.
Figure 5B:
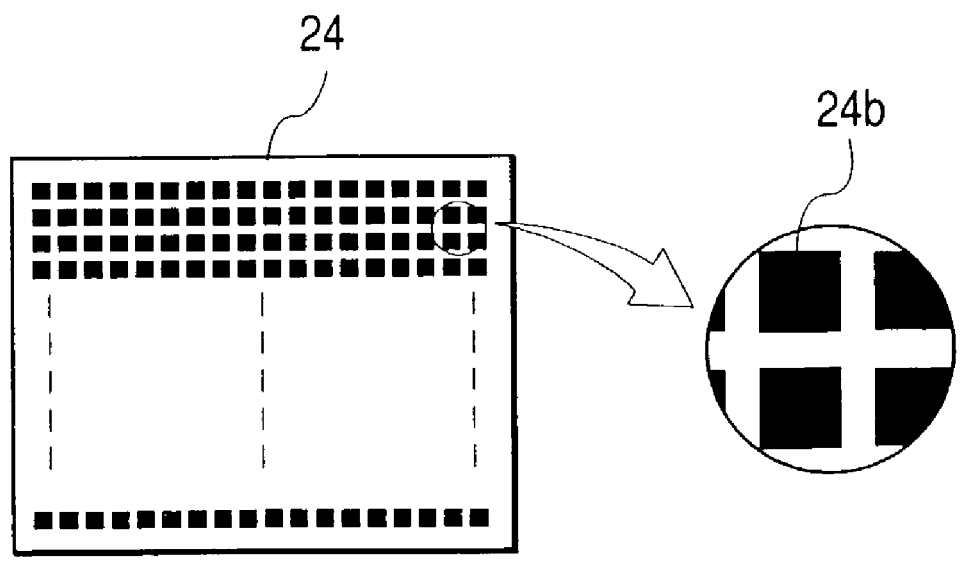
Figure 6B:
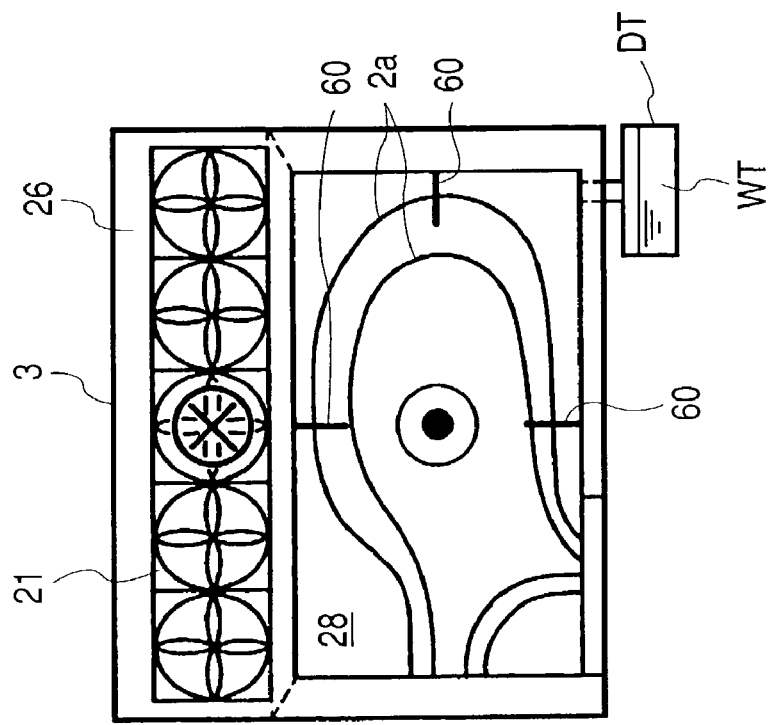
Figure 6A:
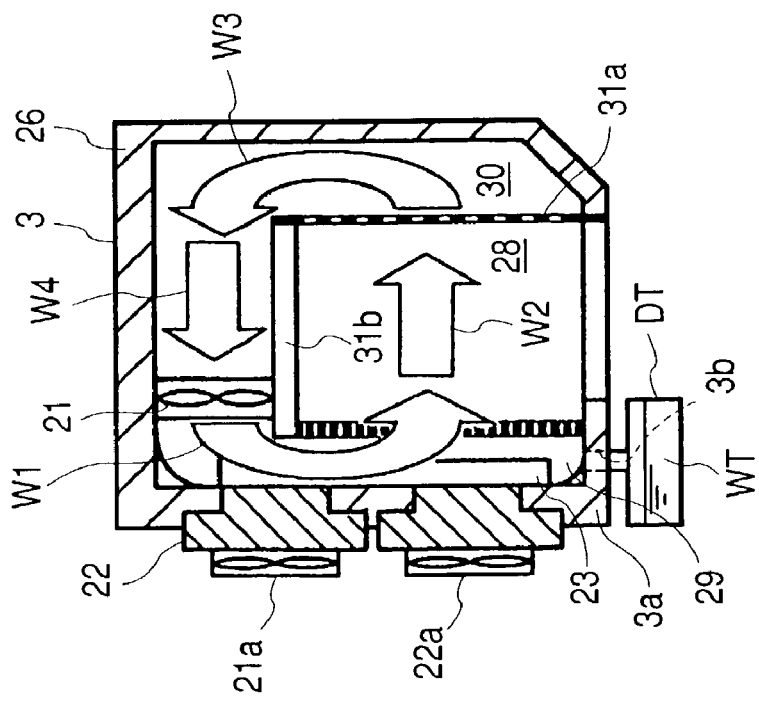
Figure 8:
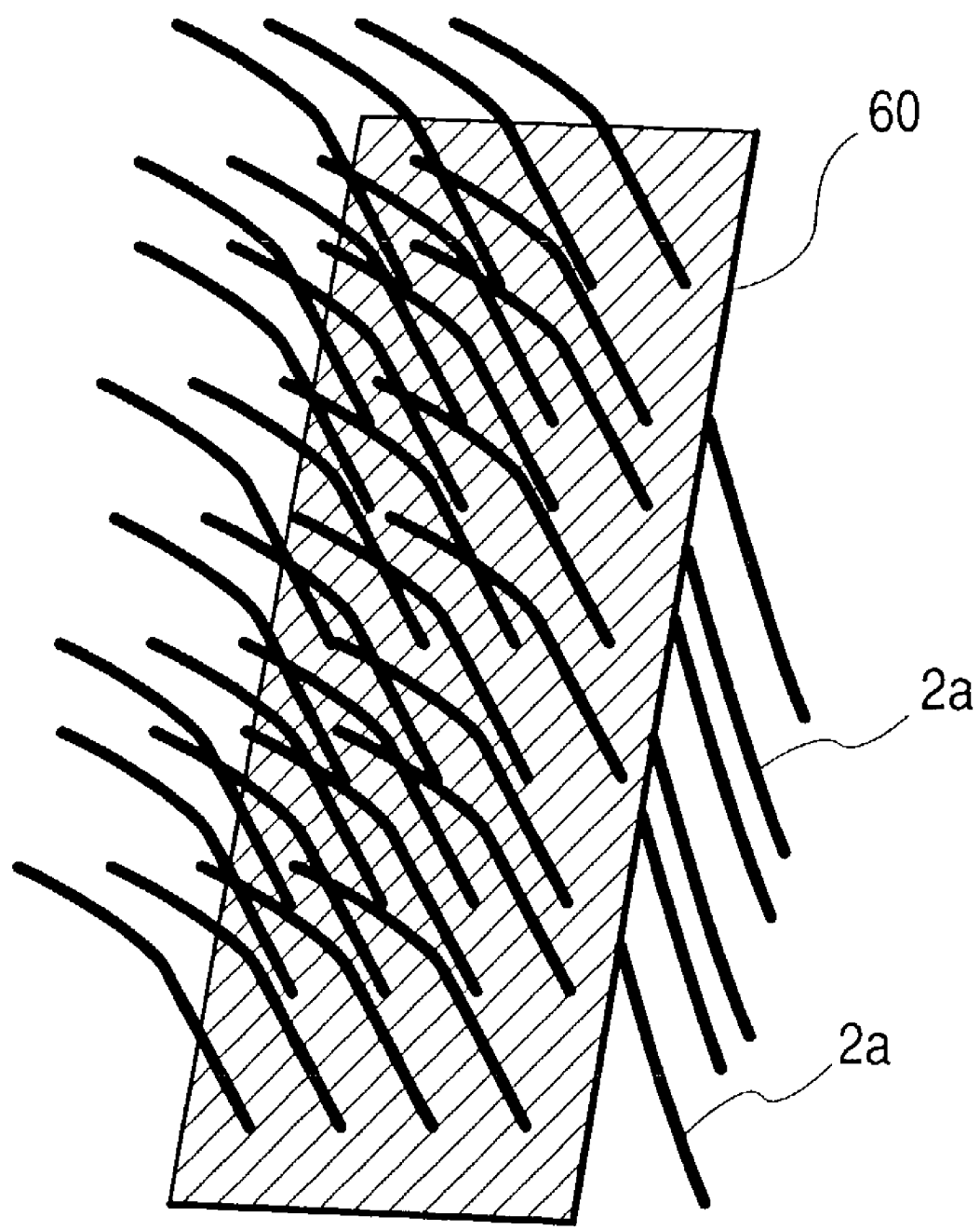
FIG. 8 is a diagram showing the structures of the plural capillaries and the separator for separately supporting the capillaries.
Figure 9A:
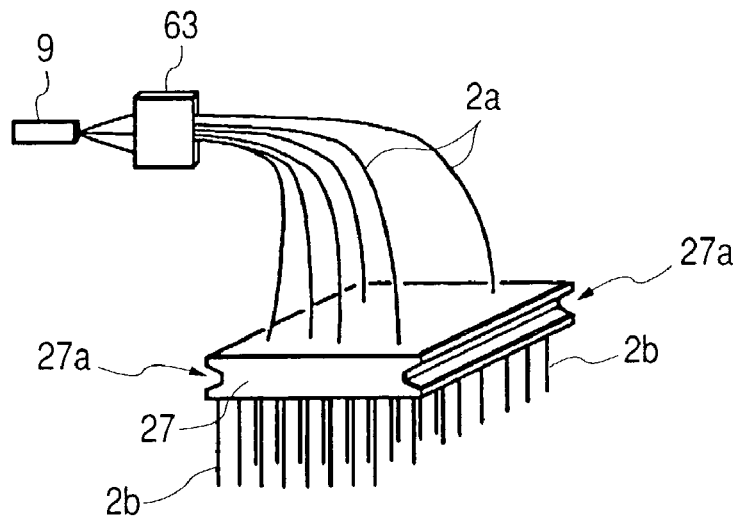
FIG. 9A is a diagram showing the structure of the load header.
Figure 9B:
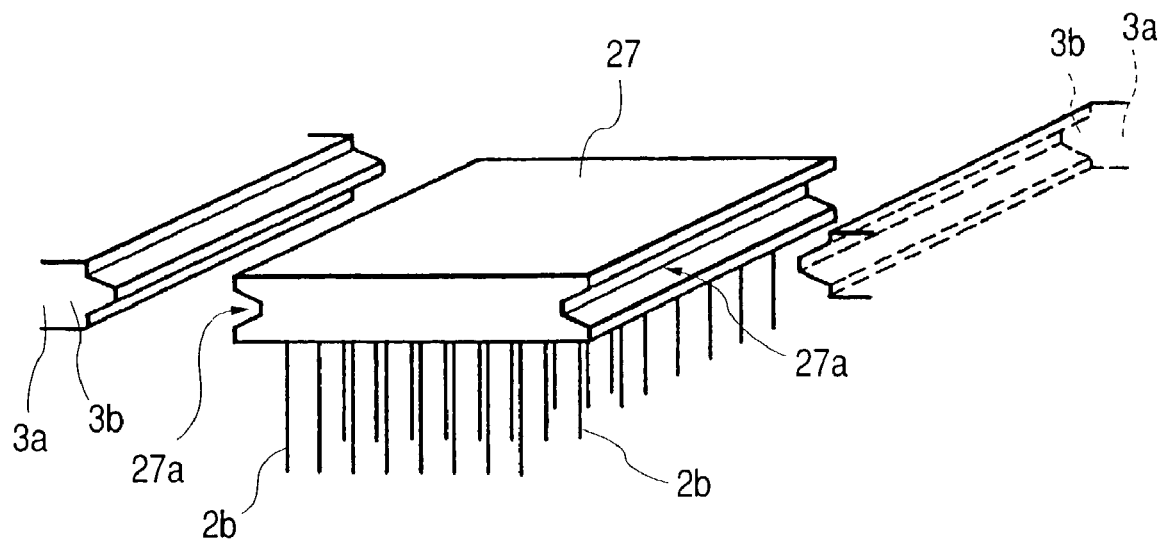
FIG. 9B is a diagram showing the structure of installation of the load header to the load header guide of the thermostat oven.

Based on the foregoing discussion, an electrophoresis apparatus according to a first embodiment of the invention will be described below with reference to FIGS. 2A to 6B and 8 to 9B. FIG. 2A is a diagram showing a structure of a capillary electrophoresis apparatus for DNA sequencing, and FIG. 2B is a diagram showing a schematic structure of a detector part for analyzing a sample. FIGS. 3A to 3C are diagrams showing structures of air thermostat ovens in the capillary electrophoresis apparatus for DNA sequencing shown in FIG. 2A, and FIG. 3A is a side cross sectional view on line IIa–IIa' in FIG. 2A. FIG. 3B is a front elevational view of the air thermostat oven, and FIG. 3C is a diagram showing a modified example of the air thermostat oven shown in FIG. 3A. FIG. 4A is a perspective view showing a fan used in the air thermostat oven and an air circulation channel, FIG. 4B is a perspective view showing a modified example of the fan, and FIG. 4C is a side elevational view showing the fan shown in FIG. 4B. FIG. 5A is a diagram showing a structure of a straightening plate, and FIG. 5B is a diagram showing a modified example of the straightening plate. FIGS. 6A and 6B are diagrams showing overviews of the air flow inside the air thermostat oven. FIG. 8 is a diagram showing the plural capillaries and a separator for separately supporting the capillaries in the capillary container part, and FIGS. 9A and 9B are diagrams showing structures of a load header supporting the capillaries at the sampling section and a load header guide.

The overall structure of the capillary electrophoresis apparatus for DNA sequencing will be firstly described.

As shown in FIGS. 2A to 3C, the multi-capillary electrophoresis apparatus for DNA sequencing 1 has a multi-capillary array 2, a thermostat oven 3, a detector part 4, a gel block 9, an electrophoresis ground 10, a electric power supply 40, and a controlling part 50.

The multi-capillary electrophoresis apparatus 1 further has a buffer tank 6, an automatic sampler 7 capable of being freely moved in the X, Y and Z directions, an array holder 8 fixing the capillary array, an electromagnetic valve 11, a syringe 12 for changing the gel, and a stacker 13 for storing samples.

The multi-capillary array 2 is constituted with plural capillaries 2a. The principal parts in the longitudinal direction of the capillaries 2a are housed in the air thermostat oven 3. The greater part of the outer peripheral wall of the air thermostat oven 3 except for a certain part is covered with a thermal insulation material 26. A heating element 22 for heating the air inside the air thermostat oven 3 is attached the certain part. Either a cooling element capable of cooling or a heating and cooling element capable of selectively heating and cooling may be provided instead of the heating element 22. Cooling fans 21a and 22a for cooling the heating element 22 are provided outside the heating element 22. Upon carrying out the measurement by electrophoresis, a cover is closed, which is attached on the front side of the air thermostat oven 3, for example, with a hinge mechanism.

A sample tray 5 for setting the sample is arranged in the vicinity of the tip end (sampling section) of the multi-capillary array 2. A buffer tank 6a, in which a buffer solution for preventing discharge upon applying a high voltage to the multi-capillary array 2 and smoothly carrying out the electrophoresis is charged, is provided in the vicinity of the sample tray 5. As the sample tray 5, for example, a commercially available microtiter plate is used. In the commercially available microtiter plate, 96 wells 5a (8 rows and 12 columns) are arranged in a matrix form. The wells 5a each actually has a cylindrical part having a cylindrical form and a taper part having a tapered part, the cross sectional shape of which is tapered from the upper side to the bottom of the sample tray 5.

The operation of charging (introduction) the sample can be conveniently carried out by providing the tapered part. The sample tray 5 and the buffer tank 6a are placed on the automatic sampler 7. The automatic sampler 7 is produced in such a manner that it can be moved within the XY plane in the X axis direction and the Y direction perpendicular thereto and can also be moved in the Z direction perpendicular to the XY plane.

The automatic sampler 7 is attached to the bottom surface of the electrophoresis apparatus 1 having a box shape and positioned in the horizontal direction and the transversal direction perpendicular thereto and in the vertical direction. The apparatus is constituted in such a manner that the automatic sampler 7 is moved to the prescribed position by controlling a moving motor (not shown in the figures) for moving the automatic sampler 7 with the controlling part 50.

The multi-capillary array 2 is formed by arranging 96 capillaries 2a (8×12), for example, in a matrix form. A separation medium (gel) for separating the sample by electrophoresis is charged in the capillaries 2a constituting the multi-capillary array 2. The ends on the side of the sample tray 5 (i.e., the side of the sampling sections) of the respective capillaries 2a are fixed with the array holder 8. The other ends of the capillaries 2a are fixed by connecting to the gel block 9.

The gel (polymer) as the separation medium is charged in the gel block 9 from the connecting part to the multi-capillary array 2 to the electrophoresis ground 10. The electric power supply 40 is connected to the ground side of the electrophoresis ground 10. The electrophoresis ground 10 is grounded in an electrically insulated state, for example, by connecting to the electrophoresis apparatus 1.

An electrode made with a metal, such as stainless steel, (not shown in the figures) is provided in the vicinities of the peripheries of the capillaries 2a and is retained with the array holder 8. Upon moving the capillaries 2a in the horizontal direction and the transversal direction perpendicular thereto and in the vertical direction, the electrode is simultaneously moved therewith. The electrode is connected to a high voltage terminal of the electric power supply 40. By using the foregoing structure, a voltage applying means for applying a voltage to the both ends of the capillaries 2a (i.e., the electrification path formed with the gel charged in the capillaries 2a) can be formed.

A detector part 4 for acquiring information depending on the sample thus separated by electrophoresis is provided in the vicinity of the end of the multi-capillary array 2. As shown in FIG. 2B, the detector part 4 has a capillary supporting part 63 formed, for example, with glass and supporting the capillaries 2a, a laser device 64, and a photo acceptance part 65 containing a photo acceptance element 65a.

The photo acceptance element 65a is, for example, a CCD solid image pickup element, and the photo acceptance part 65 is, for example, a CCD camera containing a CCD solid image pickup element. The detector part 4 is housed in a housing part 62 having a box shape shown in FIG. 2A.

The capillaries 2a are shielded from light, for example, with a black resin 2d, such as polyimide. The black resin 2d is not formed in the vicinity of the detector part 4 to form transparent window parts 2e. The laser device 64 emits laser light L, for example, to the sample in the capillaries 2a through the transparent window parts 2e. In order to suppress fluctuation in laser light intensity due to the irradiation position, two laser devices arranged vertically aligned may be provided. Excited light (fluorescence) K excited by the laser light L is detected by the CCD solid image pickup element 65a equipped in the CCD camera 65. The species of DNA is determined by the controlling part 50 based on the optical signal thus detected.

The multi-capillary electrophoresis apparatus 1 has the syringe 12 for charging the gel, by which the separation medium (gel) is exchanged per one operation of electrophoresis, and the electromagnetic valve 11 for preventing the back flow during the exchange of the gel. The controlling part 50 controls the parts of the electrophoresis apparatus 1, such as the automatic sampler 7, the electromagnetic valve 11, the syringe 12 for charging the gel, and the electric power supply 40.

As shown in FIGS. 3A to 3C, the air thermostat oven 3 equipped in the multi-capillary electrophoresis apparatus 1 according the embodiment of the invention has a two-chamber structure having a capillary housing base 28 housing the multi-capillary array 2 and a chamber part 29, 30. The chamber part has a first chamber part 29 housing the fan 21 and the heat source 22, and a second chamber part 30 forming an air circulation channel by connecting to the first chamber part 29 with the capillary housing base 28 inserted therebetween. The second chamber part 30 is formed upon closing the cover of the thermostat oven 3.

The capillary housing base 28 is formed in a first space provided by a first wall part (including parts of a first plate member 31a, a second plate member 31b, a straightening plate 24 and a thermal insulation member 26).

The chamber part 29, 30 is formed in a second space provided by the thermal insulation member 26 and the straightening plate 24 arranged between the chamber part 29, 30 and the capillary housing base 28. A temperature controlling mechanism 22, 23 for maintaining the temperature of the multi-capillary array 2 constant and the air blowing mechanism 21 for blowing the air, the temperature of which has been controlled, are provided in the chamber part 29, 30. The air blowing mechanism contains, for example, an air blowing fan 21. The temperature controlling mechanism contains, for example, a heat source 22 and a good heat conduction plate 23.

The air thermostat oven 3 has such a dimension as a width W of about 300 mm, a height H of about 360 mm and a thickness T of about 245 mm. The size of the capillary housing base 28 (the first space) housing the multi-capillary array and the conditions of the objective air circulation flow (such as the air flow velocity) are necessarily adjusted by the fan 21 and the straightening plate 24 depending on the length of the multi-capillary array 2 used. The reason for the adjustment will be described below.

A microtiter plate having 96 wells 5a is used as an example of sampling sections that cannot be arranged in the same plane, and such a case is to be described that samples are introduced from 96 (8×12) wells 5a at most to carry out analysis.

The respective wells 5a realigned, for example, with an interval of about 9 mm, and the dimension that is necessary for the sampling sections is 63×99 mm. The number of wells 5a per one row is 8 with the number of intervals being 7, and therefore, the dimension is 9×7=63 mm. In order to make the multi-capillary array 2a detachable, the multi-capillary array 2 having 96 capillaries 2a is fixed with a load header 27 having a prescribed thickness. The size of the load header 27 after fixing the multi-capillary array 2 is assumed to be a width of 72 mm and a thickness of 118 mm, and the multi-capillary array 2 is attached to the load header 27.

The aligning interval of the capillaries 2a is assumed to be the same as the aligning interval of the microtiter plate. The aligning interval of the wells 5a in the microtiter plate having 96 wells 5a is 9 mm. It is necessary, therefore, that the thickness of the capillary housing base 28 is at least 72 mm or at least 118 mm as similar to the size of the load header.

Upon arranging the detector part 4, in order that no large tension is applied to the capillaries 2a to arrange the respective capillaries 2a without contact, it is preferred that a space of about 118 mm is kept in the thickness direction of the thermostat oven. Furthermore, in order to obtain a uniform air flow velocity distribution of the air circulation flow from the straightening plate 24, it is necessary that the straightening plate 24 is kept away from the wall surface facing thereto (i.e., the thermal insulation material 26) by a prescribed distance.

The length of the capillaries 2a used is necessarily changed depending, for example, on the difference of the species of the separation medium (gel) used for electrophoresis and the purposes. In the case where the multi-capillary array 2 is arranged in a curved form as shown in FIG. 2A, the width and the height of the capillary housing base 28 are determined based on the capillary length of the longest capillary used.

The structure of the chamber part 29, 30 will be then described. The width and the height of the chamber part 29, 30 are determined based on the width and the length of the capillary housing base 28.

As shown in FIG. 3A, the heating element 22 is arranged on a back surface 29 of the chamber part (the leftward part in the figure). A heating element or a heating and cooling element is used as the heating element 22 as described in the foregoing. The heat conduction plate 23 is arranged in contact with the heating element 22 to cover the substantially entire area of the back surface of the thermostat oven 3 (the first chamber part 29). The heat conduction plate 23 has a certain heat capacity. Therefore, it has such a function that even when the temperature of the heating element 22 is fluctuated by temperature control, the temperature fluctuation is absorbed thereby to suppress temperature fluctuation of the air in the capillary housing base 28. Furthermore, heat from the heating element 22 is efficiently transferred to the interior of the first chamber 29, whereby a substantially uniform temperature distribution can be provided at every position on the back surface.

In practical, there may be temperature gradation within the plane of the heat conduction plate 23 due to influences of leakage of heat from the outer periphery of the air thermostat oven 3 and thermal conduction of the thermal insulation material 26 covering the outer periphery. Therefore, the heating element 22 is preferably a sheet form heating element that covers the entire area of the back surface of the first chamber part 29 and provides a uniform temperature distribution at every positions on the heat conduction plate 23.

A Peltier element is relatively expensive, and a Peltier element having such a size that covers the entire area of the heat conduction plate 23 by one element is not easily available. Accordingly, there is no problem when the back surface is locally covered with two Peltier elements as shown in FIG. 3A. In alternative, in the case where the back surface of the first chamber 29 has sufficient thermal insulation property to provide a substantially uniform temperature distribution on the heat conduction plate 23, the heat conduction plate 23 is arranged in the vicinity of the flowing outlet of the fan 21 to cover with only one element as shown in FIG. 3C. In order to improve the heat exchange efficiency between the heat conduction plate 23 and the air inside the first chamber 29, it is preferred that the contact area with the air is increased by attaching fins on the heat conduction plate 23.

The fan 21 is provided in the chamber part 29, 30 for forming an air circulation flow for controlling the temperature. The straightening plate 24 is provided between the first chamber part 29 and the capillary housing base 28 for flowing the air having uniform air flow direction and air flow velocity from the fan 21 to the capillary housing base 28.

As shown in FIGS. 4A and 4B, two kinds of fans may be used as the fan 21. An axial fan 21 shown in FIG. 4A aspirates the air in the direction of the rotation axis of the fan and blows the air in the direction of the rotation axis of the fan. The axial fan 21 has blade parts 21b rotating around a rotation axis 21a as the center, and a housing part 21e housing the blade parts 21b. The axial fan 21 forms a flow of the air in the direction in parallel to the rotation axis 21a. In the case where the axial fan 21 is used, the width of the capillary housing base 28 is made substantially equivalent to the width of the heat conduction plate 23. In this case, in order to prevent formation of non-uniform temperature distribution on the heat conduction plate 23, it is necessary that the width of the axial fan 21 is equivalent to the width of the capillary housing base 28.

In the case where only one of the axial fan 21 shown in FIG. 4A is used, it is necessary that the similar space as the width of the capillary housing base 28 is provided in the height direction. Therefore, as shown in FIG. 3B, it is preferred that plural fans are arranged, whereby the air is uniformly blown in the width direction of the heat conduction plate 23.

A cross flow fan 21' shown in FIGS. 4B and 4C aspirates the air in the direction perpendicular to the rotation axis 21a' of the fan 21 and blows the air in the direction perpendicular to both the aspirating direction and the rotation axis of the fan. The air can be uniformly blown in the width direction of the heat conduction plate 23 by providing the cross flow fan 21' on either the inlet of the air or the outlet of the air. In order to form a uniform flow of the air in the capillary housing base 28, it is important that the pressure distribution in the chamber part 29, 30 is made uniform, and it is preferred that the maximum static pressure of the fan is as high as possible.

In commercially available axial fans shown in FIG. 4A, there is a product having a maximum static pressure of 100 Pa or more and a maximum flow amount of 1.0 m$^3$/min or more. In the cross flow fan shown in FIG. 4B, there is a product having a maximum static pressure of 90 Pa or more and a maximum flow amount of 5.0 m$^3$/min or more. Accordingly, in the case where 5 of the axial fans shown in FIG. 4A are aligned in parallel, the air blowing performance thus obtained is equivalent to the cross flow fan.

The specification of the fan 21 is necessarily determined by the structure of the straightening plate 24 and the configuration of the air flow velocity inside the capillary housing base 28.

FIGS. 5A and 5B show the structures of the straightening plates 24. The first straightening plate 24 can change an air flow in parallel to the first straightening plate 24 in the chamber 29, 30 to an air flow perpendicular thereto. It also forms an air flow of a uniform flow direction without formation of vortex flow in the capillary housing base 28. The thermostat oven itself can be miniaturized by the function of the straightening plate. The shape and the interval of the holes and the thickness of the straightening plate 24 are designed to form a uniform air flow inside the electrophoresis part 28. FIG. 5A shows an example of the straightening plate formed by providing a large number of holes having a circular shape (shown by the black circles) on a plate. FIG. 5B shows an example thereof formed by providing a large number of holes having a tetragonal shape (shown by the black squares) on a plate. A uniform air flow is formed in the vicinity of the straightening plate 24, and thus the width of the capillary housing base 28 can be decreased. In order thereto, the interval of the holes may be decreased. However, when the interval of the holes is too small, the open area ratio of the straightening plate 24 becomes too large, and it is difficult to provide a uniform pressure distribution in the chamber. The open area ratio that is necessary for providing a uniform pressure distribution in the chamber is preferably in a range of from 5 to 50%.

Assuming that the distance from the straightening plate 24 where a uniform air flow velocity distribution can be obtained is 20 mm or more, the structure of the straightening plate is determined. The pressure loss of the fan 21 for circulating the capillary housing base 28 due to the straightening plate 24 can be estimated, and the specification of the fan 21 can be determined.

Commercially available fans generally have a maximum static pressure of about from 50 to 300 Pa, and the open area ratio of the straightening plate is appropriately changed depending on the kinds of the fan used. For example, when a fan having a maximum static pressure of 150 Pa is used, the open area ratio of the straightening plate may be from 5 to 10%. When a fan having a maximum static pressure of 70 Pa is used, the open area ratio of the straightening plate may be from 30 to 40%. The flow channel resistance and the pressure loss are changed by changing the open area ratio of the straightening plate, and the driving pressure and the air flow amount of the fan used are determined. The air flow velocity can be obtained by dividing the air flow amount by the area of the plane in the capillary housing base perpendicular to the air flow direction.

The conversion angle of the air flow direction can be determined by the open area ratio of the straightening plate. For example, the air flow direction is changed by about 90° when a fan having a high static pressure is used to maintain a certain value of air flow velocity, and the open area ratio of the straightening plate is from 5 to 10%. When a fan having a static pressure of about 70 Pa is used with the open area ratio being from 30 to 40%, the air flow direction is changed by 60 to 70°, whereby an air circulation flow that causes substantially no vortex flow can be formed in the capillary housing base.

The shapes and the positional relationship of the capillary housing base 28 and the chamber part 29, 30 are not particularly limited as far as they are in directly or indirectly contact with each other to effect heat exchange. It is preferred that the cover part 25 of the air thermostat oven has the same flow channel width as the capillary housing base 28 to prevent resistance to the flow, and the distance of the flow channel is about 20% of the height of the capillary housing base 28. A plate member having a slit S is provided between the capillary housing base 28 and the cover part 25 of the air thermostat oven. The capillary housing base 28 (the first space) and the chamber part 29, 30 (the second space) form the circulation channel of the air.

As shown in FIG. 3A, a bottom plate 3a of the thermostat oven 3 determining the first chamber part 29 has a through hole 3b. A drain tank DT connected to the through hole 3b is formed under the bottom plate 3a. Water droplets formed by dew condensation in the chamber part 29, 30 can be stored in the drain tank DT. In the case where the first chamber 29 is cooled with the Peltier element 22, it is effective to provide the drain tank because what has the lowest temperature in the thermostat oven 3 is the good thermal conduction plate 29, and dew condensation is liable to occur thereon.

Water WT formed by dew condensation can be efficiently stored into the drain tank DT by forming a slanted part (drain guide) falling toward the through hole 3b on the bottom plate 3a as shown in FIG. 3B. The water WT stored in the drain tank DT can be discarded by withdrawing the drain tank DT from the thermostat oven 3.

FIGS. 6A and 6B are figures showing an air flow in the thermostat oven 3. Five axial fans are provided each having a front size of 60×60 mm, a maximum static pressure of 100 Pa or more and a maximum air flow amount of 1.0 m$^3$/min or more. A straightening plate 24 having a dimension of 210×160 mm and a thickness of 3 mm and having a large number of holes of 1×1 mm square with an interval of the holes of 3.7 mm is used, and the conditions of air circulation in this case is shown in the figures. The air is circulated in the direction shown by the arrows.

As shown in FIG. 6A, the air flow formed by the fan 21 receives heat from the heating element 22b in a channel having a relatively large length and a small width in the first chamber 29, in which the heat conduction plate 23 is arranged, so as to form a hot air flow W1 having a prescribed temperature. The hot air flow W1 becomes a circulation flow W2 having substantially constant flow direction and flow rate upon passing the straightening plate 24. The capillaries 2a housed in the capillary housing base 28 is heated with the circulation flow W2, whereby the temperature difference in the longitudinal direction within each of the capillaries 2a can be suppressed, and simultaneously, the temperature difference in the radial direction among the plural capillaries 2a can also be suppressed.

An air flow W3 passing from the capillary housing base 28 to the second chamber part 30 through the slit becomes an air flow W4 toward the fan 21. The air flow from the fan 21 is thus circulated through the capillary housing base 28 and the chamber part 29, 30.

As shown in FIG. 6B, the plural capillaries 2a are arranged in the capillary housing base 28 to follow approximately the inner surface of the capillary housing base 28. More specifically, the plural capillaries 2a are supported by a separator 60 described later. The air flow W2 having substantially uniform flow direction and flow rate flowing from the backside of the figure toward the figure surface (FIG. 6A) is applied to the plural capillaries 2a. For example, a uniform air circulation flow having a flow velocity of about 2 m/sec can be formed in the capillary housing base 28, and thus the temperature of the capillaries 2a upon electrophoresis can be made substantially uniform.

In FIG. 6A, the white arrows show the air flow direction. In FIG. 6B, the symbol having a black dot in a white circle means a flow from the backside of the figure toward the figure surface, and the symbol having a crisscross in a white circle means a flow from the front of the figure surface toward the figure.

When the plural capillaries 2a are simply arranged in the capillary housing base 28, the capillaries 2a are liable to be in contact with each other and to be aggregated.

Particularly in the case where the multi-capillary array that cannot be housed in one plane is housed, such a part is caused that cannot receive the air flow necessary for controlling the temperature of the gel.

In order to maintain distances among the capillaries, for example, a separator 60 shown in FIG. 8 is used. The separator 60 has a large number of through holes, in which the capillaries 2a are penetrated. The capillaries 2a are supported by penetrating in the through holes to exert such functions that the capillaries 2a are retained to have certain distances among them, and vibration of the capillaries 2a caused by the air flow is suppressed. A thin plate or sheet member having heat resistance and having a large number of holes is used as the separator 60, and the multi-capillary array 2 is formed by penetrating the capillaries 2a in the holes, respectively. By using the separator 60, the plural capillaries can be aligned in the virtual flat plate having the prescribed thickness.

The through holes are preferably arranged in a staggered form. By using the staggered form arrangement, an air flow having a substantially uniform flow direction in the radial direction can be applied to the plural capillaries.

In the case where the multi-capillary array 2 formed by utilizing the separator 60 is placed in the capillary housing base 28, the separator 60 is attached in such a direction that is substantially perpendicular to the wall surface of the capillary housing base 28 to prevent the separator 60 from disturbing the air flow. The separator 60 is attached in a direction substantially perpendicular to the straightening plate 24. According to the configuration, the air flow passes in a direction in parallel with the separator 60. In other words, the air flow is headed to the thin end, and thus the separator 60 does not disturb the air flow.

For example, a circulation air flow having a flow velocity of about 2 m/sec and a uniform flow direction can be formed in the capillary housing base 28 and the chamber part 29, 30, and the temperature of the thermostat oven can also be uniformly maintained.

A load header 27 is engaged in the bottom plate (load head holder) 3a of the thermostat oven 3 defining a part of the capillary housing base 28 as shown in FIGS. 9A and 9B. The load header 27 has through holes, in which the tip ends 2b of the plural capillaries 2a are penetrated, to support the capillaries 2a by the through holes, so as to form the sampling sections 2b by the ends of the capillaries 2a protruding from the through holes. An opening is formed on the bottom plate 3a of the thermostat oven 3. The load header 27 is engaged in the opening by interdigitation. Concave portions 27a are formed on the both side surfaces of the load header 27, and on the other hand, protrusions 3b exerting interdigitation with the concave portions 27a are formed on the surfaces of the opening facing the both side surfaces of the load header 27. The concave portions 27a and the protrusions 3b are engaged by interdigitation, and thus the load header 27 can be easily installed to and uninstalled from the thermostat oven 3 by sliding like rails.

According to the constitution, maintenance can be conveniently carried out, and the sealing property of the interior of the capillary housing base 28 can be improved. Furthermore, infiltration of the outside air can be suppressed, and thus the influence of the outside air on the temperature and the air flow in the thermostat oven 3 can be suppressed.

Moreover, the reproducibility of the loaded position of the load header 27 can be improved, whereby the positions of the capillaries can also be well reproduced, and maintenance upon introducing samples can be conveniently carried out.

By using the multi-capillary apparatus according to the first embodiment of the invention, the air flow direction and the air flow velocity of the air flow applied to the capillary array can be substantially uniform. Even though the air flow velocity is not uniform, formation of vortex flow can be prevented in the capillary housing base. Therefore, the temperature difference in the longitudinal direction and the radial direction among the capillaries can be suppressed, and thus scattering on analysis can be suppressed.

A modified example of an air thermostat oven in an electrophoresis apparatus according to a modified example of the first embodiment of the invention will be described with reference to FIGS. 7A and 7B. FIG. 7A is a side cross sectional view showing the case where a cross flow fan 21' is used as the air circulation mechanism of the air thermostat oven, and FIG. 7B is an elevational view showing the case where the shape of the first space forming the capillary housing base 28 is changed from the rectangular parallelepipedal shape to such a shape that is formed by staggered combination of two rectangular parallelepipedal spaces having different positions of the bottom surfaces thereof, whereby the operation of housing the multi-capillary array 2 in the capillary housing base 28 is made convenient.

In the case where the cross flow fan 21' is used, the similar effect as in the case where the axial fan 21 is used (FIG. 6A) can be obtained with respect to the function of forming the uniform air circulation flow, and such an advantage can also be obtained that the necessary air circulation flow can be formed in the capillary housing base 28 by only one fan.

Figure 7B:
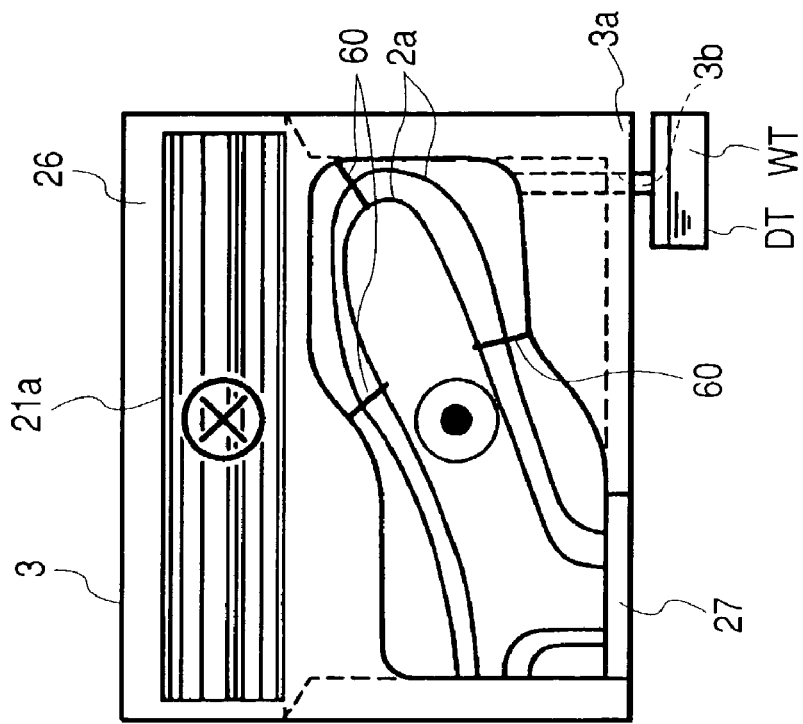
Figure 7A:
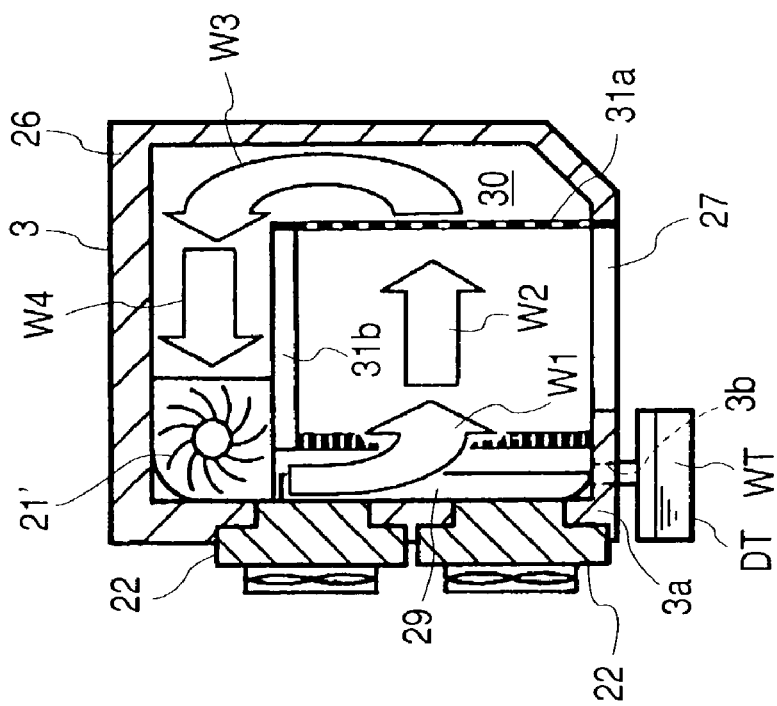

In the case where the capillaries 2a is arranged in the capillary housing base (the first space) 28 shown in FIG. 7B, a separator 60 shown in FIG. 8 is also used to retain certain distances among the capillaries.

In the multi-capillary electrophoresis apparatus, the control of the air circulation flow for uniformizing the temperature distribution in the air thermostat oven 3 can be easily carried out, for example, by a controlling device in such a manner that temperatures of prescribed positions are detected with at least one temperature sensors, based on which the electric current control of the heating or heating and cooling element is carried out.

The operation of the capillary electrophoresis apparatus according to the embodiment of the invention and the modified example thereof will be described. Samples are injected into the 96 (8×12) wells 5a of the sample tray 5 by pipetting. The cover of the air thermostat oven is closed. At this time, the outer surface except for a partial region of the air thermostat oven 3 is covered with the thermal insulation material 26. The heating and cooling element 22 capable of heating and cooling is provided on the partial region that is not covered with the thermal insulation material, and the inner surface thereof is covered with the good heat conduction member 23, whereby heat from the heating and cooling element 22 is immediately transferred to the interior of the thermostat oven. The fan 21 is activated by turning on the electric power supply. An air flow having uniform air flow velocity and air flow direction is formed in the capillary housing base 28 by the fan 21 and the straightening plate 24. The temperature in the air thermostat oven 3 is uniformized by cooperation of the thermal insulation material 26 on the outer periphery, the heating and cooling element 22 and the good heat conduction member 23. Consequently, the entire multi-capillary array 2 of the electrophoresis apparatus 1 is maintained at a constant and uniform temperature.

After obtaining such a state described in the foregoing, the automatic sampler 7 is controlled by the controlling device 50 to move the sample tray 5 in a horizontal direction. The sample tray 5 is stopped when the wells 5a of the sample tray 5 reach positions immediately below the capillaries 2a of the multi-capillary array 2. The automatic sampler 7 is then raised and stopped at such a position that the capillaries 2a are inserted in the samples in the wells 5a.

The tip ends of the capillaries 2a are inserted in the samples in the wells 5a. At this time, the electrodes provided in the vicinity of the capillaries 2a are also inserted into the samples. Under the state where they are inserted into the samples, the electric power supply 40 is operated with the controlling device 50 to apply a high voltage from the electric power supply 40 to a closed circuit formed by the electrophoresis ground 10, the gel block 9, the gel in the capillaries 2a, the testing samples, and the electrodes. The testing samples in the wells 5a are introduced into the capillaries 2a. The negative high voltage is then terminated with the controlling device 50.

The automatic sampler 7 is again moved and then stopped at such a position that the lower ends of the capillaries 2a are inserted in the buffer tank 6. The automatic sampler 7 is then moved vertically to insert the tip ends of the capillaries 2a in the buffer solution in the buffer tank 6. The electrodes are also inserted in the buffer solution. In such a state, a negative high voltage is again applied to the closed circuit formed by the electrophoresis ground 10, the gel block 9, the gel in the capillaries 2a, the testing samples, the buffer solution and the electrodes from the electric power supply 40. The samples introduced into the capillaries 2a start to exert electrophoresis by applying the high voltage and are separated within the gel (separation medium).

The gel (polymer) in the multi-capillary array 2 is replaced with fresh gel (polymer) per single measurement of electrophoresis. The electromagnetic valve 11 is closed, and the syringe 12 for charging the gel is driven, whereby the gel polymer in the syringe 12 is charged into the multi-capillary array 2 to carry out replacement of the gel.

The detector part 4 (FIG. 2B) is irradiated with laser light L for exciting the samples as described in the foregoing. Fluorescence emitted from the fluorescent reagent bonded to the DNA subjected to electrophoresis in the capillaries 2a is detected with the CCD solid image pickup element 65a to carry out analysis of the DNA with the controlling part 50.

As described in the foregoing, by using the electrophoresis apparatus according to the embodiments of the invention, the location dependency of the temperature of the air inside the thermostat oven can be suppressed, and the fluctuation of the temperature can also be suppressed. The entire capillary array upon electrophoresis can be maintained at a constant and uniform temperature. Therefore, stable separation performance can be provided upon electrophoresis analysis.

A multi-capillary electrophoresis apparatus according to a second embodiment of the invention and a modified example thereof will be described with reference to FIGS. 10A and 10B.

Figure 10A:
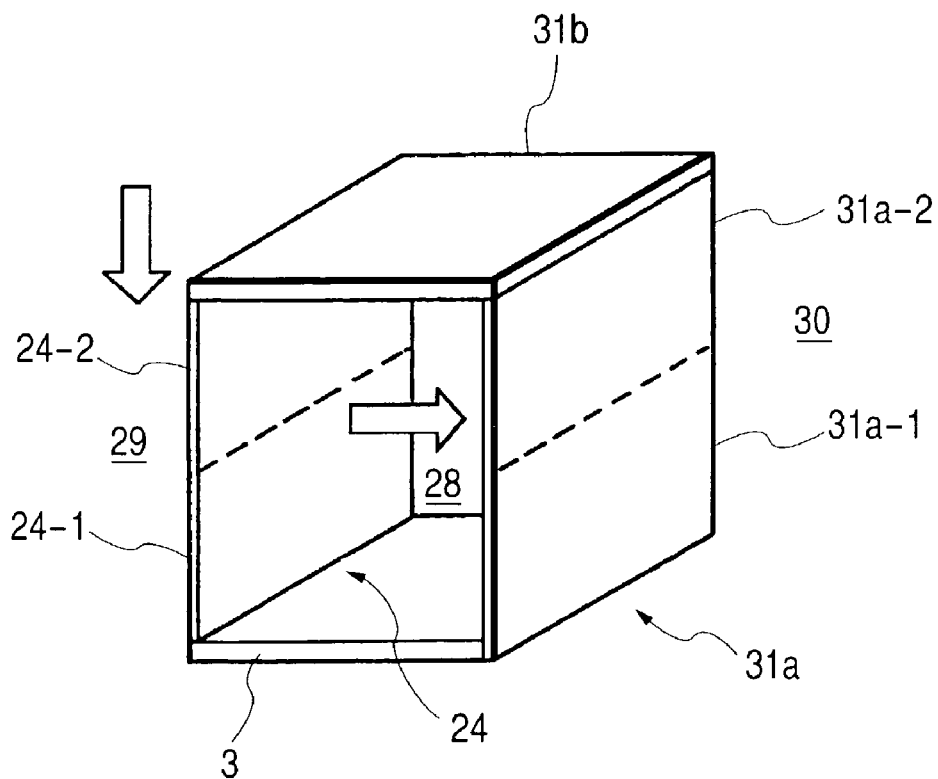
FIG. 10A is a diagram showing the arrangement of the straightening plate in the multi-capillary electrophoresis apparatus according to the second embodiment of the invention.

FIG. 10A is a diagram showing the structures of the chamber part 29, 30 and the capillary housing base 28 of the multi-capillary electrophoresis apparatus according to the second embodiment of the invention. Detailed descriptions of the other constitutional elements thereof are omitted herein because they are similar to those for the multi-capillary electrophoresis apparatus according to the first embodiment of the invention.

The arrows in the figures denote the direction of the air flow. A first straightening plate 24 can change the air flow in parallel to the first straightening plate 24 in the chamber part 29, 30 to the air flow perpendicular thereto. The first straightening plate 24 can also form an air flow having a uniform flow direction without formation of vortex flow in the capillary housing base 28. The thermostat oven itself can be miniaturized owing to these functions.

As shown in FIG. 10A, the first straightening plate 24 is arranged between the first chamber part 29 and the capillary housing base 28. The position between the first chamber part 29 and the capillary housing base 28 referred herein is not limited to the interface between them, but the first straightening plate 24 may be arranged on a air flow channel connecting the first chamber part 29 and the capillary housing base 28. In other words from another standpoint, the first straightening plate may be arranged at a position where the air flow in flows into the capillary housing base 28. In addition, a second straightening plate 31a is arranged at such a position that is between the capillary housing base 28 and the second chamber part 30 and faces the first straightening plate 24. The position between the capillary housing base 28 and the second chamber part 30 referred herein is not limited to the interface between them, but the second straightening plate 31a may be arranged on a air flow channel connecting the capillary housing base 28 and the second chamber part 30. In other words from another standpoint, the second straightening plate may be arranged at a position where the air flow outflows from the capillary housing base 28. The arrows in FIG. 10A denote the air flow direction formed by the fan. It is preferred in this case that the open area ratios of the first straightening plate 24 and the second straightening plate 31a each is changed between the upper parts and the lower parts thereof. In the first straightening plate 24 arranged on the windward side, the open area ratio of the lower part 24-1 thereof is made smaller. For example, it is preferably in a range of from 5 to 40%, and more preferably from 20 to 40%. In the first straightening plate 24, the open area ratio of the upper part 24-2 thereof is made larger than that of the lower part. For example, it is preferably in a range of from 40 to 50%.

In the second straightening plate 31a arranged in the leeward side, the open area ratio of the upper part 31a-2 thereof is made larger. For example, it is preferably in a range of from 60 to 100% (where 100% means that no straightening plate is provided). In the second straightening plate 31a, the open area ratio of the lower part 31a-2 thereof is made smaller than that of the upper part 31a-2. For example, it is preferably in a range of from 5 to 40%.

According to the foregoing constitution, the air flow direction from the windward side to the leeward side having downward tendency can be easily maintained along the normal line of the straightening plates, so as to prevent formation of vortex flow in the capillary housing base near the air blowing mechanism.

Figure 10B:
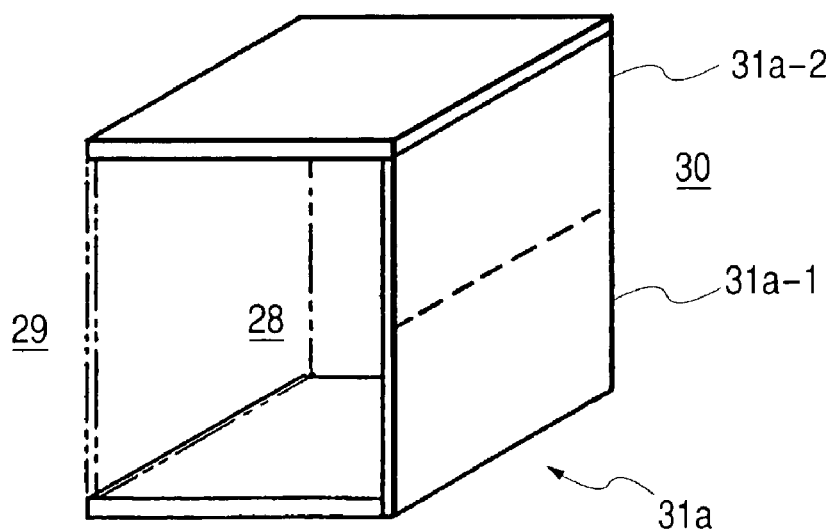
FIG. 10B is a diagram showing the arrangement of the straightening plate in the multi-capillary electrophoresis apparatus according to a modified example of the second embodiment of the invention.

As shown in FIG. 10B, the multi-capillary electrophoresis apparatus according to a modified example of the second embodiment of the invention has a third straightening plate 31a only on the leeward side of the capillary housing base 28. The third straightening plate 31a is arranged between the second chamber part 30 and the capillary housing base 28.

The straightening plate 31a is preferably formed to have such a constitution that the open area ratio of the part near the air blowing mechanism is different from that of the part remote from the air blowing mechanism. For example, the open area ratio of the part 31a-1 remote from the air blowing mechanism is in a range of from 5 to 50%, which is smaller than that of the part 31a-2 near the air blowing mechanism. The open area ratio of the part 31a-2 near the air blowing mechanism is preferably in a range of from 50 to 100%.

In the case where the structure is employed, the air flow (circulation air flow) can have a substantially uniform air flow velocity distribution when the air passing through the straightening plate 31a is again circulated.

The invention has been described with reference to the specific embodiments, but the invention is not construed as being limited thereto. It is apparent to a skilled person in the art that other various changes, improvements and combinations can be applied to the invention without deviating from the spirit thereof.

According to the invention, the resolution on electrophoresis analysis can be improved.

What is claimed is:

1. A multi-capillary electrophoresis apparatus comprising
a multi-capillary array that has a separation medium charged therein for separating a sample and has a sample injection part and a detector part for acquiring information depending on the sample thus separated,
a voltage applying mechanism for applying a voltage to an electrification path comprising the sample injection part and the detector part,
a thermostat oven that has a chamber part having an air blowing mechanism and a temperature controlling mechanism, and a capillary housing base housing at least a part of the electrification path of the multi-capillary array,
a straightening plate having plural openings that is arranged at a position where an air flow formed by the air blowing mechanism inflows into the capillary housing base, and;
wherein an open area ratio of a part of the straightening plate near the air blowing mechanism is larger than an open area ratio of a part thereof remote from the air blowing mechanism.

2. A multi-capillary electrophoresis apparatus according to claim 1, wherein the straightening plate has an open area ratio of from 5 to 50%.

3. A multi-capillary electrophoresis apparatus according to claim 1, wherein the open area ratio of the part of the straightening plate near the air blowing mechanism is from 40 to 50%, and the open area ratio of the part thereof remote from the air blowing mechanism is from 5 to 40%.

4. A multi-capillary electrophoresis apparatus according to claim 1, wherein a wall surface of the thermostat oven at a lower part of the chamber part has a bottom opening, and the apparatus further comprises a drain tank under the bottom opening.

5. A multi-capillary electrophoresis apparatus according to claim 4, wherein the apparatus further comprises, in the thermostat oven, a drain guide having a slanted part falling toward the bottom opening.

6. A multi-capillary electrophoresis apparatus according to claim 1, wherein the multi-capillary array comprises a load header, in which capillary through holes supporting the capillaries by penetrating the capillaries are arranged, and
the capillary housing base of the thermostat oven has an opening for the load header, to which the load header is engaged.

7. A multi-capillary electrophoresis apparatus according to claim 6, wherein the load header and the opening for the load header are engaged with each other by interdigitation with a protrusion and a concave portion formed therein, respectively.

8. A multi-capillary electrophoresis apparatus comprising
a multi-capillary array that has a separation medium charged therein for separating a sample and has a sample injection part and a detector part for acquiring information depending on the sample thus separated,
a voltage applying mechanism for applying a voltage to an electrification path comprising the sample injection part and the detector part,
a thermostat oven that has a chamber part having an air blowing mechanism and a temperature controlling mechanism, and a capillary housing base housing at least a part of the electrification path of the multi-capillary array,
a straightening plate having plural openings that is arranged at a position where an air flow formed by the air blowing mechanism outflows from the capillary housing base, and;
wherein an open area ratio of a part of the straightening plate near the air blowing mechanism is larger than an open area ratio of a part thereof remote from the air blowing mechanism.

9. A multi-capillary electrophoresis apparatus according to claim 8, wherein the open area ratio of the part of the straightening plate near the air blowing mechanism is from 50 to 100%, and the open area ratio of the part thereof remote from the air blowing mechanism is from 5 to 50%.

10. A multi-capillary electrophoresis apparatus according to claim 8, wherein a wall surface of the thermostat oven at a lower part of the chamber part has a bottom opening, and the apparatus further comprises a drain tank under the bottom opening.

11. A multi-capillary electrophoresis apparatus according to claim 10, wherein the apparatus further comprises, in the thermostat oven, a drain guide having a slanted part falling toward the bottom opening.

12. A multi-capillary electrophoresis apparatus according to claim 8, wherein the multi-capillary array comprise a load header, in which capillary through holes supporting the capillaries by penetrating the capillaries is are arranged, and
the capillary housing base of the thermostat oven has an opening for the load header, to which the load header is engaged.

13. A multi-capillary electrophoresis apparatus according to claim 12, wherein the load header and the opening for the load header are engaged with each other by interdigitation with a protrusion and a concave portion formed therein, respectively.

14. A multi-capillary electrophoresis apparatus comprising
- a multi-capillary array that has a separation medium charged therein for separating a sample and has a sample injection part and a detector part for acquiring information depending on the sample thus separated,
- a voltage applying mechanism for applying a voltage to an electrification path comprising the sample injection part and the detector part,
- a thermostat oven that has a chamber part having an air blowing mechanism and a temperature controlling mechanism, and a capillary housing base housing at least a part of the electrification path of the multi-capillary array,
- a first straightening plate having plural openings that is arranged at a position where an air flow formed by the air blowing mechanism inflows into the capillary housing base,
- a second straightening plate having plural openings that is arranged at a position where an air flow formed by the air blowing mechanism outflows from the capillary housing base, and;
- wherein an open area ratio of a part of the first straightening plate near the air blowing mechanism is larger than an open area ratio of a part thereof remote from the air blowing mechanism.

15. A multi-capillary electrophoresis apparatus according to claim 14, wherein the first straightening plate has an open area ratio of from 5 to 50%.

16. A multi-capillary electrophoresis apparatus according to claim 14, wherein the open area ratio of the part of the first straightening plate near the air blowing mechanism is from 40 to 50%, and the open area ratio of the part thereof remote from the air blowing mechanism is from 5 to 40%.

17. A multi-capillary electrophoresis apparatus according to claim 14, wherein
- a wall surface of the thermostat oven at a lower part of the chamber part has a bottom opening, and
- the apparatus further comprises a drain tank under the bottom opening.

18. A multi-capillary electrophoresis apparatus according to claim 17, wherein the apparatus further comprises, in the thermostat oven, a drain guide having a slanted part falling toward the bottom opening.

19. A multi-capillary electrophoresis apparatus according to claim 14, wherein
- the multi-capillary array comprises a load header, in which capillary through holes supporting the capillaries by penetrating the capillaries are arranged, and
- the capillary housing base of the thermostat oven has an opening for the load header, to which the load header is engaged.

20. A multi-capillary electrophoresis apparatus according to claim 19, wherein the load header and the opening for the load header are engaged with each other by interdigitation with a protrusion and a concave portion formed therein, respectively.

21. A multi-capillary electrophoresis apparatus, comprising
- a multi-capillary array that has a separation medium charged therein for separating a sample and has a sample injection part and a detector part for acquiring information depending on the sample thus separated,
- a voltage applying mechanism for applying a voltage to an electrification path comprising the sample injection part and the detector part,
- a thermostat oven that has a chamber part having an air blowing mechanism and a temperature controlling mechanism, and a capillary housing base housing at least a part of the electrification path of the multi-capillary array,
- a first straightening plate having plural openings that is arranged at a position where an air flow formed by the air blowing mechanism inflows into the capillary housing base,
- a second straightening plate having plural openings that is arranged at a position where an air flow formed by the air blowing mechanism outflows from the capillary housing base, and;
- wherein an open area ratio of a part of the second straightening plate near the air blowing mechanism is larger than an open area ratio of a part thereof remote from the air blowing mechanism.

22. A multi-capillary electrophoresis apparatus according to claim 21, wherein the open area ratio of the part of the second straightening plate near the air blowing mechanism is from 50 to 100%, and the open area ratio of the part thereof remote from the air blowing mechanism is from 5 to 50%.

23. A multi-capillary electrophoresis apparatus according to claim 21, wherein the first straightening plate has an open area ratio of from 5 to 50%.

24. A multi-capillary electrophoresis apparatus according to claim 20, wherein
- a wall surface of the thermostat oven at a lower part of the chamber part has a bottom opening, and
- the apparatus further comprises a drain tank under the bottom opening.

25. A multi-capillary electrophoresis apparatus according to claim 24, wherein the apparatus further comprises, in the thermostat oven, a drain guide having a slanted part falling toward the bottom opening.

26. A multi-capillary electrophoresis apparatus according to claim 21, wherein
- the multi-capillary array comprises a load header, in which capillary through holes supporting the capillaries by penetrating the capillaries are arranged, and
- the capillary housing base of the thermostat oven has an opening for the load header, to which the load header is engaged.

27. A multi-capillary electrophoresis apparatus according to claim 26, wherein the load header and the opening for the load header are engaged with each other by interdigitation with a protrusion and a concave portion formed therein, respectively.

28. A multi-capillary electrophoresis apparatus comprising
- a multi-capillary array that has a separation medium charged therein for separating a sample and has a sample injection part and a detector part for acquiring information depending on the sample thus separated,
- a voltage applying mechanism for applying a voltage to an electrification path comprising the sample injection part and the detector part,
- a thermostat oven that has a chamber part having an air blowing mechanism and a temperature controlling mechanism, and a capillary housing base housing at least a part of the electrification path of the multi-capillary array in a virtual flat plate, a separator plate attached in the capillary housing base for supporting the plural capillaries in the virtual flat plate to separate the plural capillaries by prescribed distances, a straightening plate provided substantially perpendicular to the separator plate, and;

wherein an open area ratio of a part of the straightening plate near an upstream side of the air flow in the horizontal direction is larger than an opening area ratio of a part thereof remote from the upstream side.

29. A multi-capillary electrophoresis apparatus comprising a multi-capillary array that has a separation medium charged therein for separating a sample and has a sample injection part and a detector part for acquiring information depending on the sample thus separated, a voltage applying mechanism for applying a voltage to an electrification path comprising the sample injection part and the detector part, a chamber part having an air blowing mechanism and a temperature controlling mechanism, and a capillary housing base housing at least a part of the electrification path of the multi-capillary array, the multi-capillary electrophoresis apparatus further comprising a thermostat oven having an air flow channel formed by the chamber part and the capillary housing base, and a straightening plate preventing formation of vortex flow in the capillary housing base.

30. A multi-capillary electrophoresis apparatus according to claim 29, wherein an open area ratio of a part of the straightening plate near an upstream side of the air flow in the horizontal direction is larger than an opening area ratio of a part thereof remote from the upstream side.

31. A multi-capillary electrophoresis apparatus comprising a multi-capillary array that has a separation medium charged therein for separating a sample and has a sample injection part and a detector part for acquiring information depending on the sample thus separated, a voltage applying mechanism for applying a voltage to an electrification path comprising the sample injection part and the detector part, a thermostat oven that has a chamber part having an air blowing mechanism for forming an air flow and a temperature controlling mechanism for controlling a temperature of the air flow, and a capillary housing base housing at least a part of the electrification path of the multi-capillary array, and a straightening plate having plural openings, through which the air flow passes, the straightening plate changing an air flow direction of the air flow in a horizontal direction with respect to the straightening plate to an air flow in a perpendicular direction with respect to the straightening plate.

32. A multi-capillary electrophoresis apparatus according to claim 31, wherein an open area ratio of a part of the straightening plate near an upstream side of the air flow in the horizontal direction is larger than an opening area ratio of a part thereof remote from the upstream side.

* * * * *